United States Patent [19]
Mori

[11] Patent Number: 5,993,779
[45] Date of Patent: Nov. 30, 1999

[54] METHOD FOR PRODUCING NON-HUMAN ANIMAL HAVING SPINAL CORD INJURY

[76] Inventor: Atsuo Mori, Rejidensu TOYOUKE Tsuruta 203, 2810-9, Tsurutamachi, Utsunomiya-shi, Tochigi-ken, Japan

[21] Appl. No.: 08/919,367

[22] Filed: Aug. 28, 1997

[30] Foreign Application Priority Data

Oct. 14, 1996 [JP] Japan ..................................... 8-271092

[51] Int. Cl.[6] .......................... A61M 31/00; A01N 37/12; A61K 49/00
[52] U.S. Cl. ............................. 424/9.2; 604/53; 600/562; 600/595; 514/561; 424/9.2
[58] Field of Search .............................. 424/9.2; 514/561; 600/309; 800/9

[56] References Cited

PUBLICATIONS

Seibel et al. Journal of Vascular Surgery, vol. 18, No. 2 pp. 153–160, Aug. 1993.
Ogata et al., Journal of Orthopaedic Research, 14:504–510, May 1996.
Gill et al., Brain Research, 580: 35–43, 1992.
Faden et al., European Journal of Pharmacology, 175: 165–174, Jan. 1990.
Yum, S. W. and Faden, A. I., Arch Neurol, vol. 47, pp. 277–281, Mar. 1990.
Mangano, R. M. and Schwarcz, R., Brain Research Bulletin, vol. 10, pp. 47–51, 1983.
Richard M. Mangano and Robert Schwarcz, Chronic Infusion of Endogenous Excitatory Amino Acids into Rat Striatum and Hippocampus, Brain Research Bulletin, vol. 10, pp. 47–51, 1983.
R.F. Regan and D.W. Choi, Glutamate Neurotoxicity in Spinal Cord Cell Culture, Neuroscience, vol. 43, No. 2/3, pp. 585–591, 1991.
P. Scott Seibel, MD, Pierre Theodore, BS, Irving L. Kron, MD, and Curtis G. Tribble, MD, Regional adenosine attenuates postischemic spinal cord injury, Journal of Vascular Surgery, vol. 18, No. 2, pp. 153–160, Aug. 1993.
Neurology, vol. 39 (Suppl1), pp. 371–372, Mar. 1989.

*Primary Examiner*—Bruce R. Campell
*Assistant Examiner*—Shin-Lin Chen
*Attorney, Agent, or Firm*—Sughrue, Mion, Zinn, Macpeak & Seas, PLLC

[57] ABSTRACT

A method for producing a non-human animal suffering from a spinal cord injury, which comprises interrupting an aorta at least at two sites, thereby forming an isolated segment of the aorta including branched parts of radicular arteries feeding the spinal cord between the sites of interruption, bringing the spinal cord to ischemia, and regionally administering glutamic acid or aspartic acid to the segment and a method for evaluating a medicament for treating a spinal cord injury due to glutamic acid or aspartic acid, which comprises interrupting an aorta of a non-human animal at least at two sites, thereby forming an isolated segment of the aorta including branched parts of redicular arteries feeding the spinal cord between the sites of interruption, bringing the spinal cord to ischemia, and regionally administering glutamic acid or aspartic acid together with a medicament for treating a spinal cord injury to the segment or a method for evaluating a medicament for treating a spinal cord injury due to glutamic acid or aspartic acid, which comprises administering a medicament for treating a spinal cord injury to a non-human animal produced according to the above method.

10 Claims, 5 Drawing Sheets

METHOD FOR PRODUCING NON-HUMAN
ANIMAL HAVING SPINAL CORD INJURY

BACKGROUND OF THE INVENTION

1) Field of the Invention

The present invention relates to a method for producing an animal suffering from a spinal cord injury such as paraplegia, etc. due to the neurotoxicity of glutamic acid or aspartic acid and also a method for evaluating a medicament for treating a spinal cord injury, which can protect nerves by attenuating the neurotoxicity of glutamic acid or aspartic acid.

2) Description of Related Art

Spinal cord injury such as paraplegia, etc. is a serious complication of thoracoabdominal aortic aneurysm operation, and particularly the prevalence of postoperative paraplegia has been reported to range from 5% to 20%, depending on the site and extent of the aortic aneurysm and the presence or absence of aortic dissection. Numerous improvements of surgical operative techniques and pharmacological spinal cord protections have been proposed for preventing occurrence of paraplegia, but no methods have been established yet for completely avoiding this dreadful complication.

That is, it has been desired to make studies on the clarification of complicated pathophysiologic mechanism and causes of the disease as to the spinal cord injury such as paraplegia, etc. and also to make studies on development, etc. of medicaments for treating the disease, particularly studies on provision of test animals suffering from spinal cord injury such as paraplegia, etc. due to a specific cause of disease and also on provision of a method for evaluating medicaments targeted at the specific cause of disease. Up to now, it has been reported that nerve degeneration and paraplegia occur in spinal cords of rabbits subjected to infrarenal aortic isolation for 15 to 20 minutes (MARTINEZ-ARIZALA, A., J, B. LONG, D. D. RIGGAMONTI, J. M. KRAIMER, et al, 1989, Deteriorating stroke model of spinal ischemia in the rabbit is associated with a marked hyperemia, Neurology 39 (Suppl 1): 371–372), but the rabbits have not been clarified yet as to the causes for paraplegia, etc., and thus are not always to serve as preferable test animals for the above-mentioned evaluation purpose.

On the other hand, it has been recently clarified that glutamic acid and aspartic acid, which are major excitatory neurotransmitters that are abundant in the central nerve system, including the spinal cord, are potentially neurotoxic to central nerve cells (neurons) and are involved in the pathophysiologic mechanism of a variety of neuronal diseases. Furthermore, it is (now) presumed that the neurotoxicity of glutamic acid and aspartic acid takes part in the spinal cord injury such as paraplegia, etc.

Regan and Choi reported that neuro-degeneration occurred in vitro in spinal cord cell cultures of rats when exposed to a glutamic acid solution. However, the neurotoxicity of glutamic acid was not directly demonstrated in vivo. According to Mangano and Schwarcz, no nerve injury was observed even when a 300 mM glutamic acid solution was infused into the hippocampus for two weeks at a rate of 0.5 $\mu$l/hr. That is, no animals suffering from a spinal cord injury such as paraplegia, etc. due to exogenous glutamic acid or aspartic acid have not been obtained up to now.

SUMMARY OF THE INVENTION

An object of the present invention is to provide an animal suffering from paraplegia due to glutamic acid or aspartic acid as one of factors for causing a spinal cord injury such as paraplegia, etc., and a method for evaluating a medicament for treating the spinal cord injury due to glutamic acid or aspartic acid, using such animals.

The present invention relates to a method for producing a non-human animal suffering a spinal cord injury, which comprises interrupting an aorta at least at two sites, thereby forming an isolated segment of the aorta including branched parts of radicular arteries feeding the spinal cord between the sites of interruption, bringing the spinal cord to ischemia, and regionally administering glutamic acid or aspartic acid to the segment. Furthermore, the present invention relates to a method for evaluating a medicament for treating a spinal cord injury due to glutamic acid or aspartic acid, which comprises interrupting an aorta of a non-human animal at least at two sites, thereby forming an isolated segment of the aorta including branched parts of radicular arteries feeding the spinal cord between the sites of interruption, bringing the spinal cord to ischemia, and regionally administering glutamic acid or aspartic acid to the segment, and a method for evaluating a medicament for treating a spinal cord injury due to glutamic acid or aspartic acid, which comprises administering a medicament for treating a spinal cord injury to the non-human animal suffering from the spinal cord injury produced by the above-mentioned method.

PREFERRED EMBODIMENTS OF THE INVENTION

Figure 1:
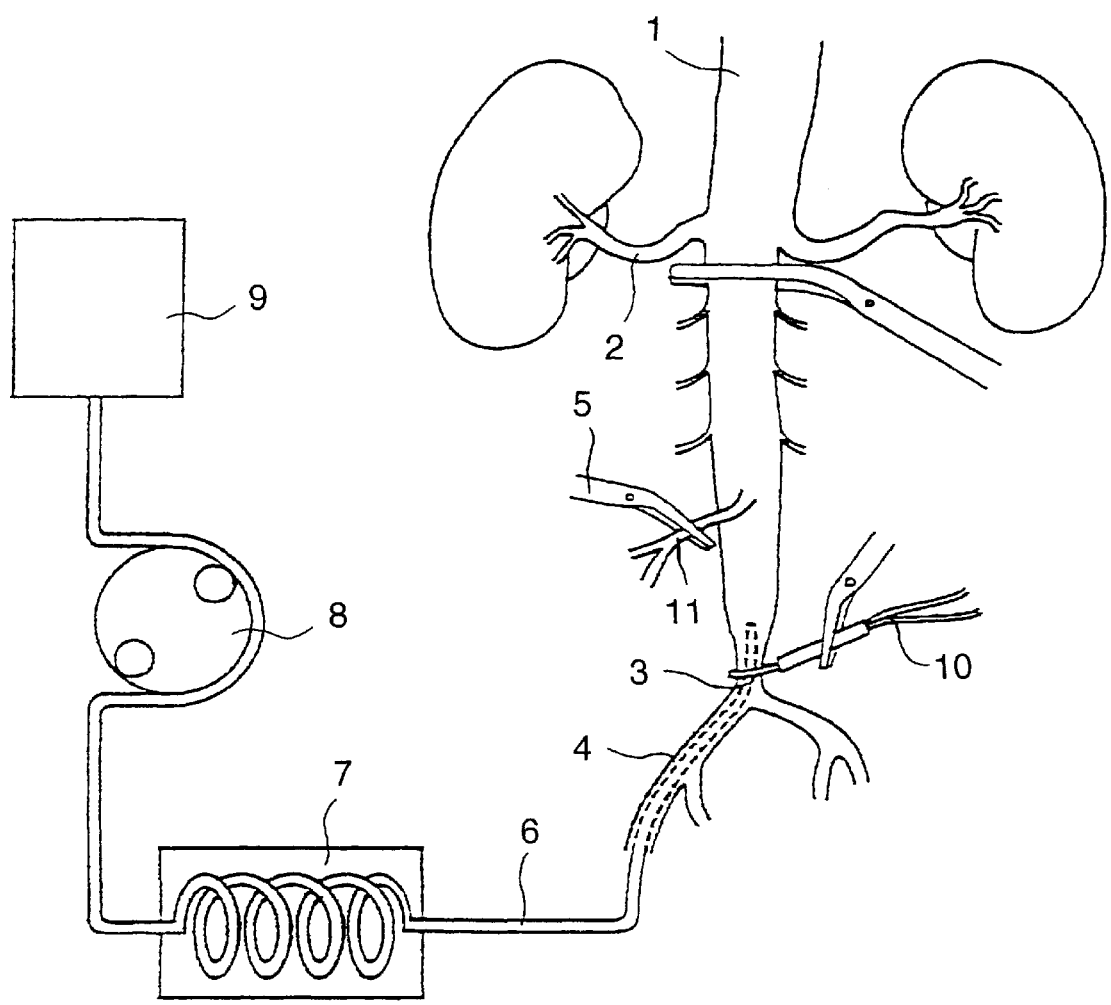
FIG. 1 shows a mode of surgical operation of an abdominally dissected rabbit according to one embodiment of the present method.

In the present invention, the term "spinal cord injury" refers to a paraplegia, paraparesis, neurodegeneration, etc. In the present invention, the term "aorta" refers to such an aorta in a region where radicular arteries feeding the spinal cord are branched, and depends on animal species, for example, the abdominal aorta in case of rabbits and the thoracic aorta in case of dogs and pigs. In the present invention, the term "radicular arteries" refers to arteries that supply blood to organs. In the present invention, the term "sites" of "at least at two sites" refers to sites of interruption or clamp of aorta, between which a segment of the aorta is formed by the interruption or clamp, including branched parts of radicular arteries feeding the spinal cord. When the segment formed by the isolation contains other blood vessels than the radicular arteries feeding the spinal cord, it is preferable to interrupt such blood vessels. Glutamic acid or aspartic acid for use in the present invention includes salts thereof, such as sodium salt, potassium salt, etc. In the administration of glutamic acid or aspartic acid, concentration and administration time of glutamic acid or the like can be selected as desired, but administration time may be a duration of time that the ischemia itself may not cause a nerve injury and, interruption of the aorta for a long duration of time may induce other factors than due to glutamic acid or aspartic acid, for example, a plurality of factors such as a low oxygen concentration, a low perfusion, aggregation of platelets, etc., and thus it is preferable to administer a solution of glutamic acid or aspartic acid for such a short duration of time that other factors may contribute only minimally to spinal cord injury. In the present invention, the term "non-human animal" refers to all the animals other than human beings, preferably, rabbits, rats, cats, dogs, pigs and monkeys. In the present invention, the term "medicament for treating a spinal cord injury" refers to a drug directed to treatment of a spinal cord injury due to glutamic acid or aspartic acid, for example, antagonistic drugs such as N-methyl-D-aspartic acid (NMDA) receptor, non-N-methyl-D-aspartic acid (non-NMDA) receptor, etc. all of which are also glutamic acid receptors; drugs taking part in glutamic acid transporter, which mainly act to extracellularly remove glutamic acid to lower the extracellular concentration of glutamic acid, etc. Specific examples thereof include NBQX (2,3-dihydroxy-6-nitro-7-sulfamoyl-benzo(f)-guinoxaline), which is a selective inhibitor for α-amino-3-hydroxy-5-methylisoazole-4-propionic acid/kainate (AMPA/kainate) receptor, one of non-NMDA receptors, etc. The term "regional administration" refers to infusion of a glutamic acid solution; an antagonist drug, etc. through a catheter kept to stay in the segment formed by the isolation, according to which a small dose of a medicament solution having a high tissue concentration can be administered into the spinal cord, while maintaining the ischemia. This refers preferably to the administration disclosed in Seibel PS, Theodore P, Kron IL, Tribble CG, Regional adenosine attenuates postischemic spinal cord injury J Vasc Surg 1993; 18:153–60.

One embodiment of the present invention will be described below, referring to rabbits as test animals on the basis of FIG. 1, which is only illustrative and not limitative of the present invention.

(1) Method for producing animals suffering from a spinal cord injury due to glutamic acid or aspartic acid (i) A rabbit is subjected to general anesthesia, then placed supine to make a median laparotomy, and then the abdominal aorta 1 is dissected just inferior to the renal vein 2 and just above the bifurcation 3. After intravenous injection of heparin, a catheter 6 is introduced from the femoral artery 4 to the abdominal aorta 1.

(ii) A glutamic acid solution or aspartic solution 9 having a concentration of 20 mM or more is infused through the catheter 6 after adjusted to physiologic osmolarity. At the same time, the abdominal aorta is clamped with a vascular clip 5 inferior to the renal vein 2, and the catheter 6 introduced from the femoral artery is externally snared by a tape 10 around the abdominal aorta at the bifurcation to interrupt the blood flow, as shown in FIG. 1. Care should be paid not to choke the infusion catheter by too strong snaring of the tape 10. The posterior mesenteric artery 11 is also clamped with a vascular clip 5. The glutamic acid solution or aspartic acid solution is pumped by a pump 8 and warmed to 39° C. through a heater 7 and infused into the isolated segment for 3 to 5 minutes. In the control group, a physiological saline solution 9 is infused likewise at the same infusion rate in place of the glutamic acid solution or the like. After the infusion, the clamps 5 are released and the tape around the bifurcation is loosened to restart the blood flow. The infusion catheter 6 is removed and the abdominal walls are closed in two layers.

(iii) At a specific time after the operation, neurologic observations of hindlimbs are evaluated according to the Tarlov's modified score.

After fixation with formalin and HE (hematoxylin-eosin) staining, Luxol-fast-blue staining and Nissl staining, histopathologic assessment using light microscope is conducted for evaluation.

(2) Method for evaluating a medicament for treating a spinal cord injury due to glutamic acid or aspartic acid (a) Control group is prepared in the same manner as the test group in the above-mentioned method (1), whereas the test group is prepared by the same method as in the above-mentioned method (1) except that a medicament whose medical effect on the treatment of a spinal cord injury is tested is infused in addition to the glutamic acid solution or the aspartic acid solution having a concentration of 20 mM or more, which is to be infused into the test group in the above-mentioned method (1). The same neurologic observations and histopathologic assessment as in the above-mentioned method (1) are conducted, and the efficacy of the medicament on the treatment of the spinal cord injury is investigated by comparison of the results of the test group with those of the control group.

When the appearance of spinal cord injury as mentioned in the method (1) is significantly inhibited by a medicament for treating the spinal cord injury, the medicament is evaluated to have an efficacy in the treatment.

(b) Both control group and test group are prepared as in the test group in the method (1), a medicament, whose medical effect on the treatment of spinal cord injury is evaluated, is administered to the test group, whereas a physiological saline solution is administered to the control group. Evaluation is to be made as in (a). In (b), medicament administration route is not particularly limited. For example, any administrative route can include intravenous injection, subcutaneous injection, intramuscular injection, intraperitoneal administration, intraspinal administration, etc.

The method (a) is advantageous in increased regional concentration of a medicament in the spinal tissues, even if administered in a small dose, because the medicament administration route is the same as the infusion route of glutamic acid or the like.

The present invention will be described in detail below, referring to Example.

EXAMPLE 1

New Zealand white rabbits weighing 3.5 to 4.0 kg were used, and subjected to general anesthesia by inhalation of 1.5% halothane and 98.5% oxygen without any premedication. Animals were then placed supine and subjected to surgical operation under spontaneous breathing without any assisted aspiration using endotracheal intubation or mechanical ventilation. A venous catheter (24 gauge) was placed in an ear vein, and cefazolin (10 mg/kg) was intravenously injected. Arterial pressure was continuously monitored in the central ear artery and rectal temperature was continuously monitored as a body temperature. A heating pad was used to maintain the body temperature of animals. Under sterile conditions, a median laparotomy was made. The abdominal aorta was dissected just inferior to the renal vein and just above the bifurcation. For anticoagulation, heparin sulfate (60 U/kg) was intravenously injected and then a 20-gauge catheter with a guide wire was introduced from the right femoral artery to the abdominal aorta. The tip of this catheter, which could be seen through the aorta, was fixed to the position of 5 mm above the bifurcation of the aorta.

Group A rabbits received infusion of 50 mM glutamic acid solution, which was adjusted to physiologic osmolarity with sodium chloride and distilled water, through the catheter inserted into the femoral artery. At the same time, the abdominal aorta was clamped with a vascular clip immediately inferior to the left renal vein. The catheter inserted from the femoral artery was externally snared by a tape around the bifurcation of the abdominal aorta, as shown in FIG. 1, to interrupt blood flow. The posterior mesenteric artery was also clamped with a vascular clip. The glutamic acid solution was warmed to 39° C. by a heater and infused into the isolated segment at a rate of 2 ml/min. for 5 minutes. Group B rabbits (control group to group A) likewise received infusion of physiological saline solution at the same rate in place of the glutamic acid solution. After 5 minutes, the clamps were released and the snare around the bifurcation was loosened to restart blood flow and at the same time to discontinue the infusion. The infusion catheter was removed and the abdominal walls were closed in two layers. The rabbits were allowed free access to water and food after awakening from the anesthesia. Group C rabbits were pretreated with segmental infusion of NBQX (4 mg/kg) (which was purchased from Tocris Cockson Ltd. and dissolved in 0.9% NaCl and adjusted to a concentration of 4 mg/ml) administered through a catheter inserted from the femoral artery over 2 minutes, followed by infusion of 30 mM glutamic acid solution delivered at a rate of 2 ml/min. for 4 minutes through the femoral arterial catheter. Group C rabbits were then subjected to the same test as in the above-mentioned method and, after closing of the abdominal walls, received a continuous intravenous infusion of NBQX (0.1 mg/kg per hour) over 6 hours after the operation to effect reduction. This administration protocol was used to exclude the paradoxical neuropathic effects of NBQX resulting from glutamic acid receptor up-regulation. Group D rabbits received segmental infusion of only the vehicle used for NBQX pretreatment through the femoral arterial catheter over 2 minutes as the control group to group C, followed by infusion of 30 mM glutamic acid solution administered at a rate of 2 ml/min. for 4 minutes through the femoral arterial catheter in the same manner as in group C. The group D rabbits were then subjected to the same test as in the above-mentioned method and, after the surgical operation, received continuous infusion of only the vehicle excluding NBQX over 6 hours.

Neurologic and histopathologic evaluation

Neurologic findings of hindlimbs were evaluated at 12, 24 and 48 hours after operation using the modified Tarlov score system (0=paraplegia, 1=paraparesis, 2=sits with assistance, 3=sits without assistance, 4=weak hop and 5=complete recovery). After 48 hours from the operation, animals were reanesthetized, followed by laparotomy and catheter insertion as in the first operation. The animals were sacrificed with an overdose of intravenously administered pentobarbital. The spinal cords were perfusion-fixed by infusing a 10% formalin solution into the isolated segment. Spinal cord was extirpated together with spines and immersed in a 10% formalin solution for 2 weeks and fixed. The extracted spinal cord was cross-sectioned from the lumbosacral cord and stained with HE, Luxol-fast blue and Nissl and subjected to histopathologic study using light microscope. Histologic findings were assessed by the neuropathologist, who was blinded to the results of neurologic findings. All the tests were carried out according to the guideline on Care and Use of Laboratory Animals by NIH. Comparison of the postoperative neurologic findings between the test group and the control group was made by statistical analysis using Mann-Whitney U test.

Five of 7 rabbits in group A exhibited paraplegia (Tarlov score of 0) at 12, 24 and 48 hours after the operation. Two rabbits showed paraparesis (Tarlov score of 1) at all the time points. All 7 rabbits in group B recovered into a neurologically normal state (Tarlov score of 5) at all the time points (Table 1). Group A rabbits had a statistically less significant neurologic score than group B rabbits (P<0.001).

Three of 6 rabbits in group C recovered fully at 48 hours. The other 3 rabbits exhibited a mild to moderate disturbance in motor function at 48 hours. Three of 6 rabbits in group D exhibited paraplegia (Tarlov score of 0) and one rabbit showed paraparesis (Tarlov score of 1) (Table 1). Group C rabbits had a statistically more significant neurologic score than group D rabbits (p<0.0039).

Figure 2A:
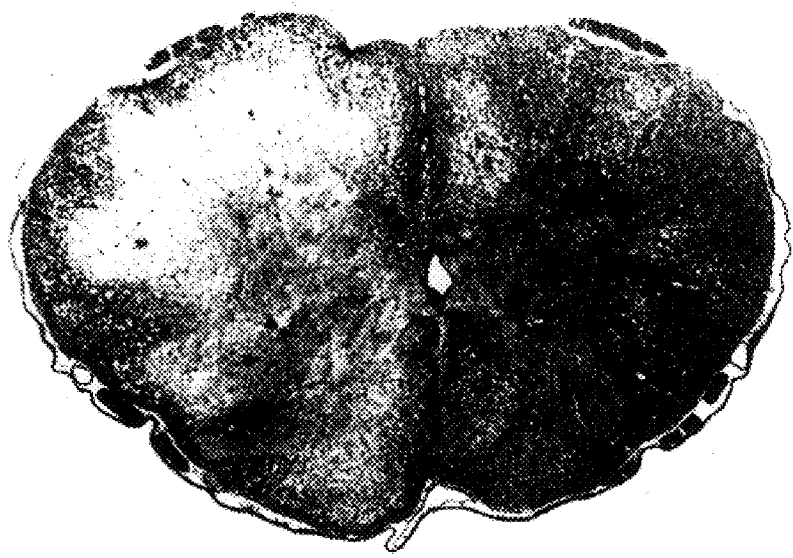
FIG. 2A is a photomicrograph (x 25) showing the histologic section of spinal cord in group A of Example 1.
Figure 2B:
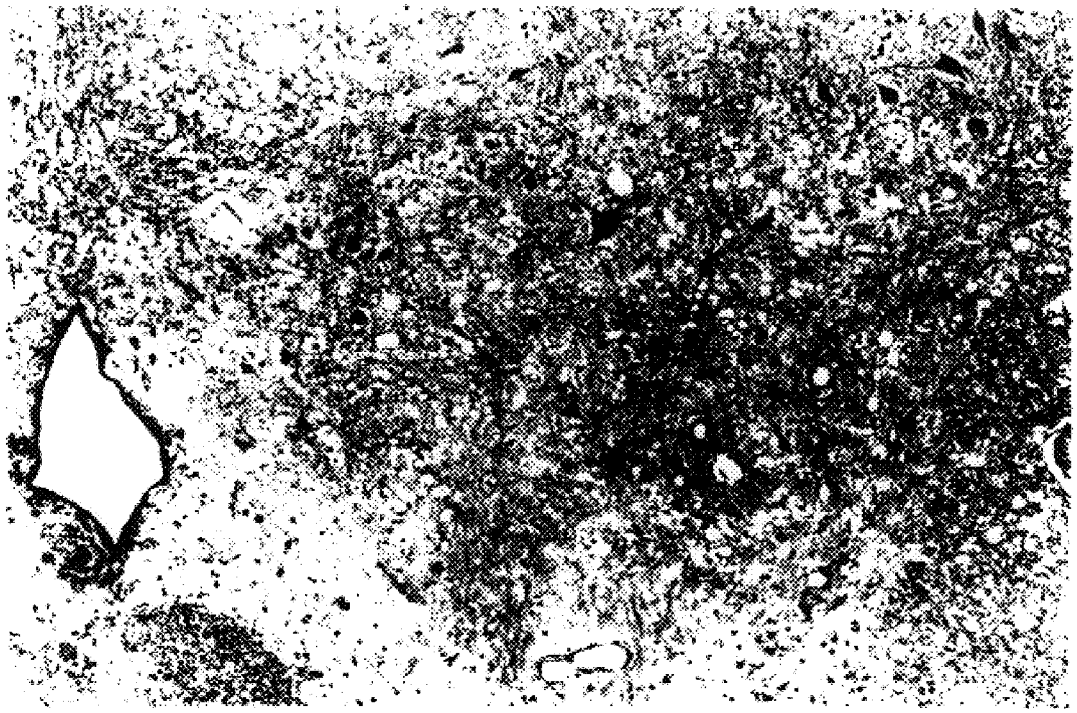
FIG. 2B is a photomicrograph (x 125) showing the histologic section of spinal cord in group A of Example 1.
Figure 3A:
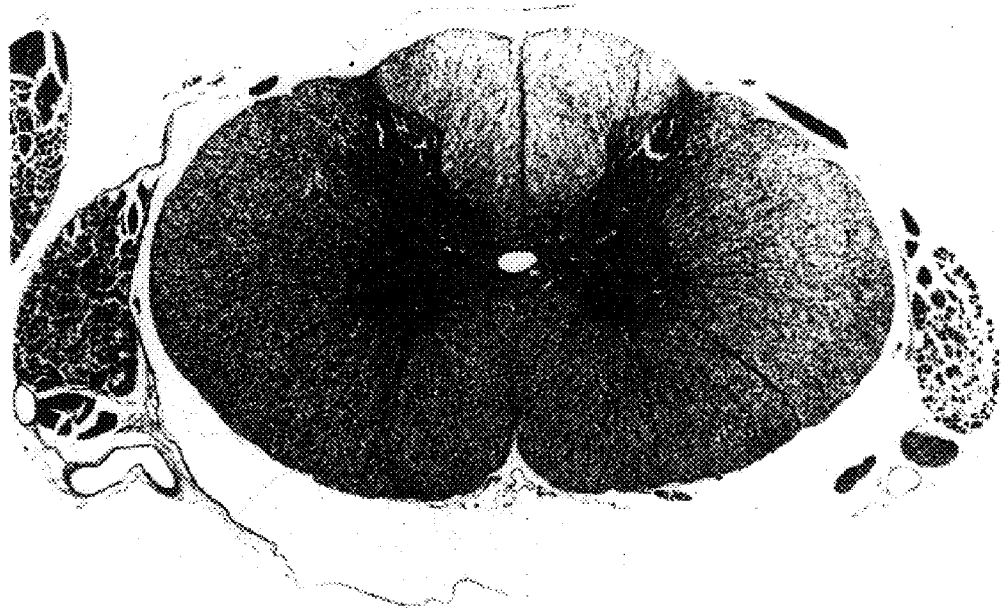
FIG. 3A is a photomicrograph (x 25) showing the histologic section of spinal cord in group B of Example 1.
Figure 3B:
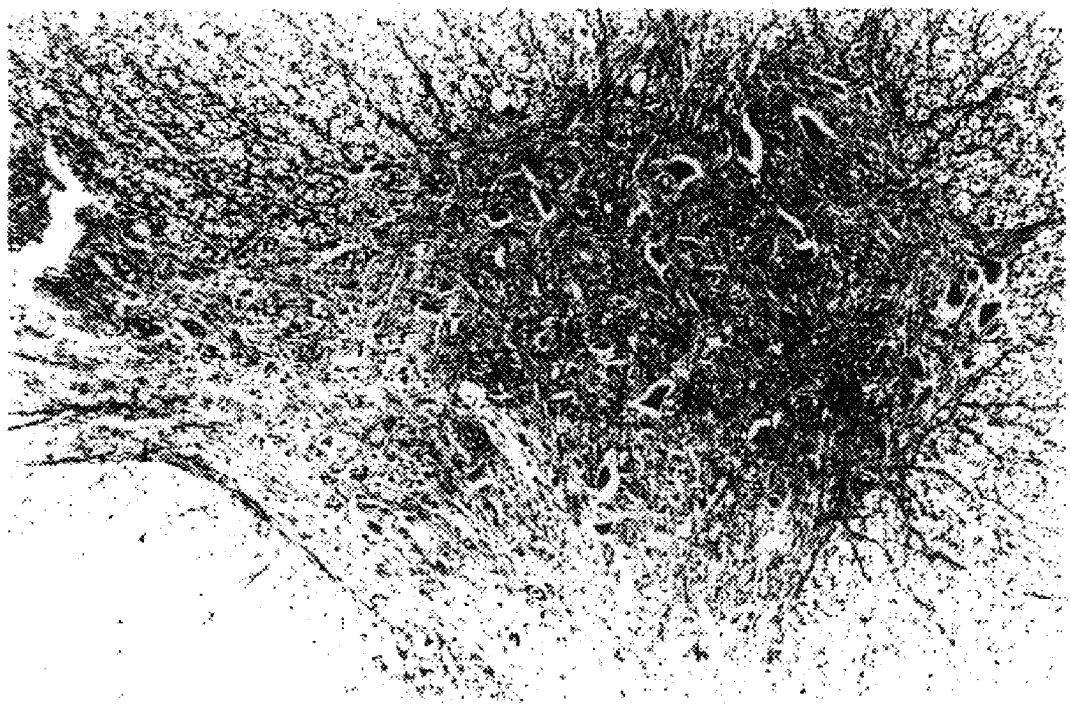
FIG. 3B is a photomicrograph (x 125) showing the histologic section of spinal cord in group B of Example 1.
Figure 4A:
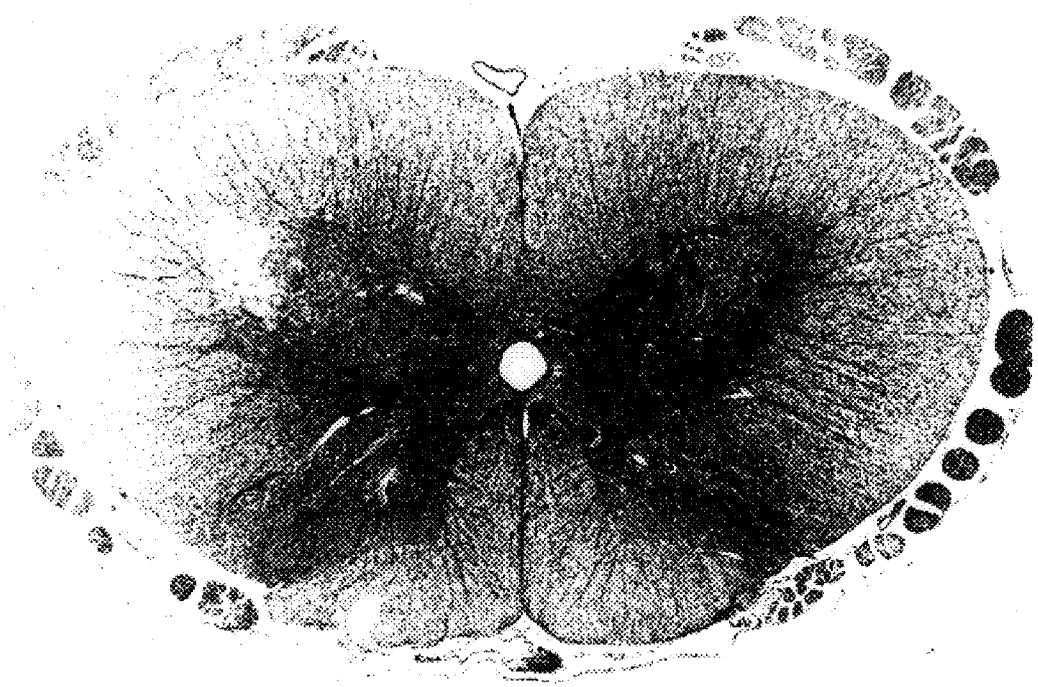
FIG. 4A is a photomicrograph (x 25) showing the histologic section of spinal cord in group C of Example 1.
Figure 4B:
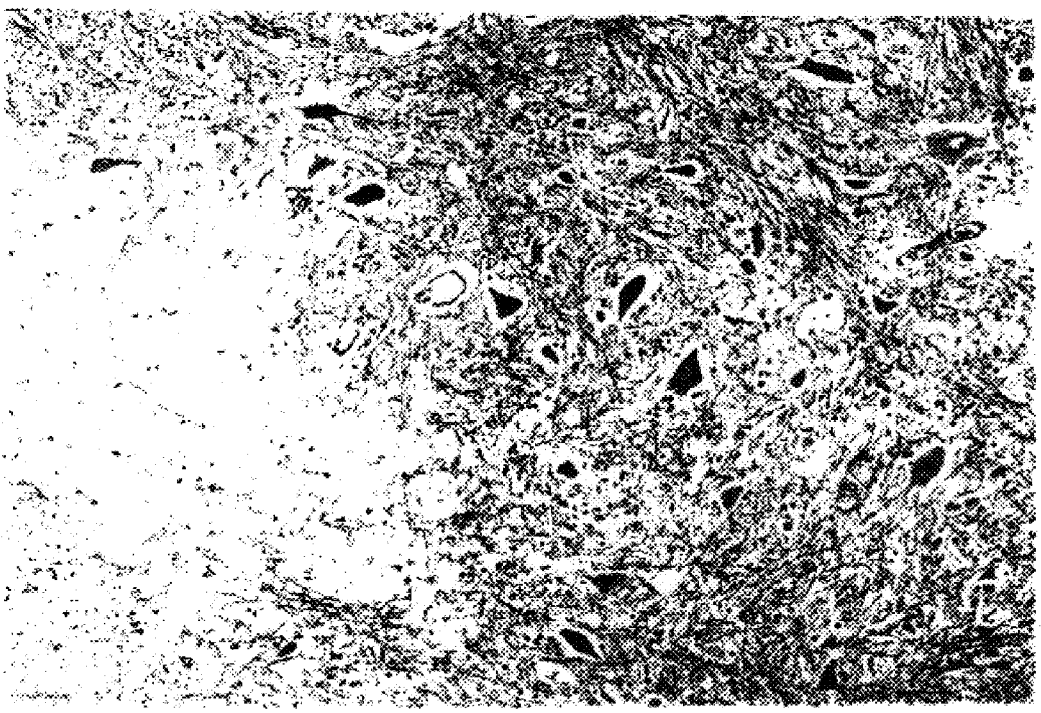
FIG. 4B is a photomicrograph (x 125) showing the histologic section of spinal cord in group C of Example 1.

Histopathologic studies showed severe and extensive gray matter necrosis with vascular necrosis in the anterior and dorsal horns throughout all the lumbosacral cords extirpated from group A. White matter degeneration was noted around the severe gray matter necrosis in group A (FIGS. 2A and 2B). It was confirmed that paraplegia occurred even with 20 mM glutamic acid solution in the same method in preliminary tests. On the other hand, in group B, a normal histologic appearance was maintained in all the spinal cords (FIGS. 3A and 3B). In group C, a mild change with cavitation, hyperchromatic nuclei, eosinophilic change, etc. was observed as localized in the anterior horns in the sacral cord. There was no white matter degeneration in group C (FIGS. 4A and 4B).

Figure 5A:
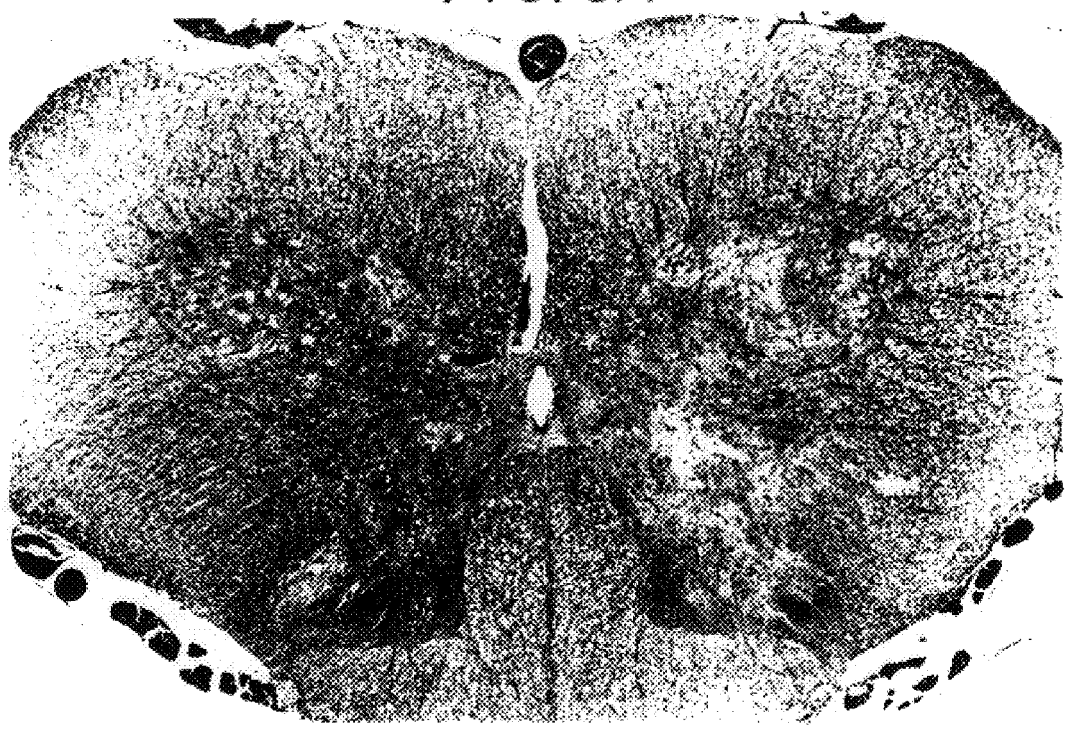
FIG. 5A is a photomicrograph (x 25) showing the histologic section of spinal cord in group D of Example 1.
Figure 5B:
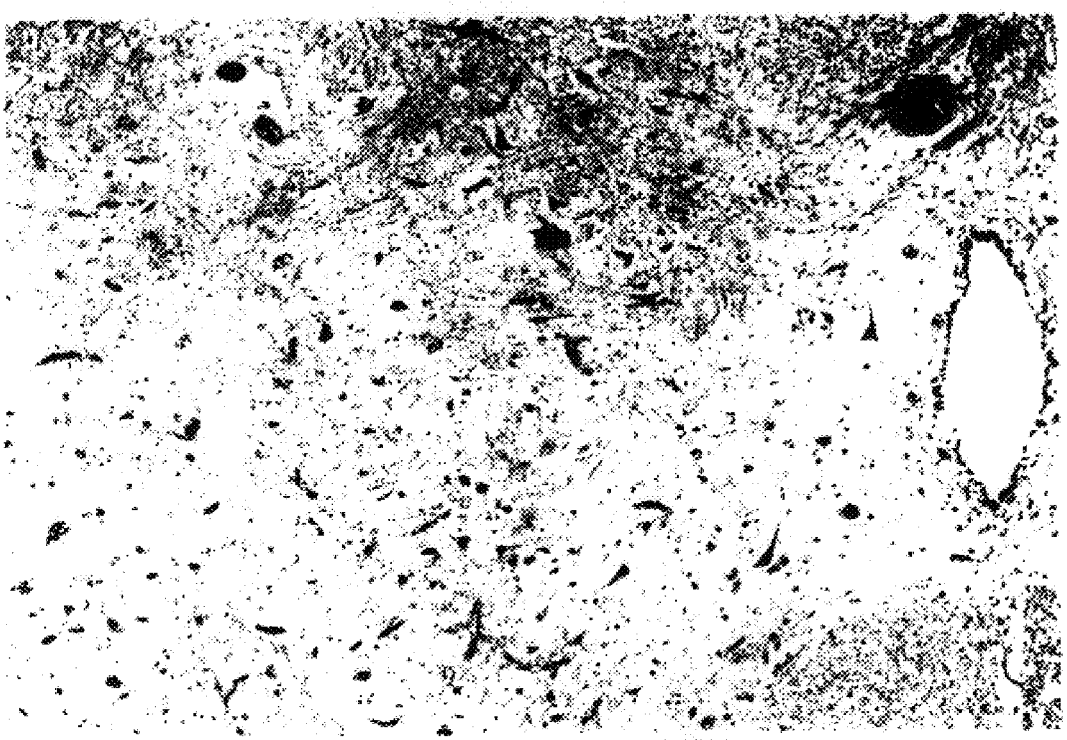
FIG. 5B is a photomicrograph (x 125) showing the histologic section of spinal cord in group D of Example 1.

On the other hand, in group D gray matter necrosis was observed in the anterior and posterior horns. White matter was maintained as compared with the gray matter, and limited white matter degeneration was localized only around the severe gray necrosis (FIGS. 5A and 5B).

Rectal temperature immediately before the aortic clamping had no significant differences each between group A and group B and between group C and group D. No significant differences were also found between the groups in the systematic mean blood pressure and pulse rate during the aortic clamping (Table 2).

TABLE 1

| Tarlov score | Group A (n = 7) | | | Group B (n = 7) | | | Group C (n = 6) | | | Group D (n = 6) | | |
|---|---|---|---|---|---|---|---|---|---|---|---|---|
| | 12 h | 24 h | 48 h | 12 h | 24 h | 48 h | 12 h | 24 h | 48 h | 12 h | 24 h | 48 h |
| 0 | 5 | 5 | 5 | 0 | 0 | 0 | 0 | 0 | 0 | 3 | 3 | 3 |
| 1 | 2 | 2 | 2 | 0 | 0 | 0 | 0 | 0 | 0 | 1 | 1 | 1 |
| 2 | 0 | 0 | 0 | 0 | 0 | 0 | 0 | 0 | 0 | 2 | 2 | 2 |
| 3 | 0 | 0 | 0 | 0 | 0 | 0 | 2 | 2 | 2 | 0 | 0 | 0 |
| 4 | 0 | 0 | 0 | 0 | 0 | 0 | 1 | 1 | 1 | 0 | 0 | 0 |
| 5 | 0 | 0 | 0 | 7 | 7 | 7 | 3 | 3 | 3 | 0 | 0 | 0 |

TABLE 2

| | Group A | Group B | Group C | Group D |
|---|---|---|---|---|
| Body temperature (°C.) | 38.7 ± 0.3 | 38.8 ± 0.3 | 39.4 ± 0.4 | 38.9 ± 0.5 |
| Mean arterial blood pressure (mmHg) | 56.4 ± 4.4 | 58.0 ± 9.3 | 57.5 ± 6.7 | 57.5 ± 5.0 |
| Heart beat rate (/min.) | 302 ± 13 | 304 ± 18 | 288 ± 24 | 297 ± 26 |

Test animals produced according to the present method and the present method for evaluation are much distinguished in evaluation of medical efficacy of a medicament for inhibiting a neuronal injury due to glutamic acid or aspartic acid. Particularly owing to a very short time of aortic isolation, other factors than glutamic acid or aspartic acid are advantageously suppressed to a minimum.

What is claimed is:

1. A method for producing a non-human mammal suffering from a spinal cord injury, which comprises interrupting an aorta at least at two sites, thereby forming an isolated segment of the aorta including branched parts of radicular arteries feeding the spinal cord between the sites of interruption, bringing the spinal cord to ischemia, and regionally administering a glutamic acid solution or aspartic acid solution to the segment for such a duration of time that the ischemia itself may not cause a nerve injury.

2. A method according to claim 1, wherein the glutamic acid solution or aspartic acid solution is a glutamic acid solution or aspartic acid solution having a concentration of 20 mM or more.

3. A method according to claim 1, where the mammal is a rabbit, a rat, a cat, a dog, a pig or a monkey.

4. A method for evaluating a medicament for treating and/or preventing a spinal cord injury due to glutamic acid or aspartic acid, which comprises interrupting an aorta of a non-human mammal at least at two sites, thereby forming an isolated segment of the aorta including branched parts of radicular arteries feeding the spinal cord between the sites of interruption, bringing the spinal cord to ischemia, and regionally administering a glutamic acid solution or aspartic acid solution to the segment for such a duration of time that the ischemia does not cause nerve injury, before and/or thereafter administering to said mammal a medicament for treating and/or preventing a spinal cord injury and evaluating the effect of said medicament on said spinal cord injury by making neurological observations of hindlimbs of said mammal according to Tarlov's modified score, or by making a histopathological assessment of the spinal cord of said mammal.

5. A method according to claim 4, wherein the glutamic acid solution or aspartic acid solution is a glutamic acid solution or aspartic acid solution having a concentration of 20 mM or more.

6. A method for evaluating a medicament for treating a spinal cord injury due to glutamic acid or aspartic acid, which comprises administering a medicament for treating a spinal cord injury to a mammal produced according to a method of claim 1, and evaluating the effect of said medicament on said spinal cord injury by making neurological observations of hindlimbs of said mammal according to Tarlov's modified score, or by making a histopathological assessment of the spinal cord of said mammal.

7. A method for evaluating a medicament for treating a spinal cord injury due to glutamic acid or aspartic acid, which comprises administering a medicament for treating a spinal cord injury to a mammal produced according to a method of claim 2, and evaluating the effect of said medicament on said spinal cord injury by making neurological observations of hindlimbs of said mammal according to Tarlov's modified score, or by making a histopathological assessment of the spinal cord of said mammal.

8. A method for evaluating a medicament for treating a spinal cord injury due to glutamic acid or aspartic acid, which comprises administering a medicament for treating a spinal cord injury to a mammal produced according to a method of claim 3, and evaluating the effect of said medicament on said spinal cord injury by making neurological observations of hindlimbs of said mammal according to Tarlov's modified score, or by making a histopathological assessment of the spinal cord of said mammal.

9. A method according to claim 4, wherein the mammal is a rabbit, a rat, a cat, a dog, a pig or a monkey.

10. A method according to claim 6, wherein the mammal is a rabbit, a rat, a cat, a dog, a pig or a monkey.

* * * * *